United States Patent
Mikhail

[19]

[11] Patent Number: 5,925,051
[45] Date of Patent: Jul. 20, 1999

[54] METHOD AND APPARATUS FOR POSITIONING AND COMPACTING BONE GRAFT

[76] Inventor: W.E. Michael Mikhail, 4203 Shamley Green, Toledo, Ohio 43623

[21] Appl. No.: 09/002,419

[22] Filed: Jan. 2, 1998

Related U.S. Application Data

[63] Continuation-in-part of application No. 08/787,140, Jan. 22, 1997, Pat. No. 5,718,707.

[51] Int. Cl.$^6$ .................................................. A61B 17/56
[52] U.S. Cl. .............................................. 606/94; 600/93
[58] Field of Search ................................ 606/94, 95, 93, 606/92, 86; 604/181, 187

[56] References Cited

U.S. PATENT DOCUMENTS

| | | |
|---|---|---|
| 4,274,408 | 6/1981 | Nimrod . |
| 4,337,773 | 7/1982 | Raftopoukos et al . |
| 4,338,925 | 7/1982 | Miller . |
| 4,341,206 | 7/1982 | Perrett et al. . |
| 4,399,814 | 8/1983 | Pratt, Jr. et al. . |
| 4,623,353 | 11/1986 | Buechel et al. . |
| 4,678,471 | 7/1987 | Nobel et al. . |
| 4,686,972 | 8/1987 | Kurland . |
| 4,706,659 | 11/1987 | Matthews et al. . |
| 4,751,922 | 6/1988 | DiPietropolo . |
| 4,815,454 | 3/1989 | Dozier, Jr. . |
| 4,846,161 | 7/1989 | Roger . |
| 4,860,735 | 8/1989 | Davey et al. . |
| 4,865,608 | 9/1989 | Brooker, Jr. . |
| 4,873,969 | 10/1989 | Huebsch . |
| 4,881,536 | 11/1989 | Nobel et al. . |
| 4,896,662 | 1/1990 | Noble . |
| 4,919,153 | 4/1990 | Chin . |
| 4,919,673 | 4/1990 | Willert et al. . |
| 4,919,679 | 4/1990 | Averill et al. . |
| 4,963,155 | 10/1990 | Lazzeri et al. . |
| 4,986,826 | 1/1991 | Roger . |
| 4,994,065 | 2/1991 | Gibbs et al. . |

(List continued on next page.)

FOREIGN PATENT DOCUMENTS

| | | |
|---|---|---|
| 2615097 | 5/1987 | France . |
| 0 315 283 | 11/1988 | United Kingdom . |
| 92/03993 | 3/1992 | WIPO . |

OTHER PUBLICATIONS

Kenneth J. Hock, M.D., "Economy is the Mother of a Cement Removal Technique", *Orthopedics Today*, pp. 18–19.

John N. Install, M.D., et al., "Principles and Techniques of Knee Replacement", published in 1983 by New York Society for the Relief of the Ruptured and Crippled, pp. 20–21.

John Insall, M.D. and Albert H. Burstein, Ph.D., "Insall/Burstein™ Total Knee System" Pamphlet.

W.E. Michael Mikhail, M.D. and Lars Weidenhielm, M.D., "The CPT Hip Prosthesis" Pamphlet (1994).

Osteonics Restoration Cemented Hip System For Revision Surgery, 4 pages.

Waldes Truarc Retaining Rings, Jan. 1981, p. 5 (Selector Guide).

*Primary Examiner*—Guy V. Tucker
*Attorney, Agent, or Firm*—Emch, Schaffer, Schaub & Porcello, Co., L.P.A.

[57] ABSTRACT

A method and apparatus for introducing and compacting bone graft material in an enlarged femoral cavity including a dispenser having a barrel containing bone graft material and a cannulated ejector/compactor positionable over a multi-section guide wire for both ejecting bone graft material from the barrel and compacting the bone graft material while being guided on the guide wire. The ejector/compactor has a modular head which may be removed and replaced by other heads of varying size.

24 Claims, 14 Drawing Sheets

U.S. PATENT DOCUMENTS

| | | |
|---|---|---|
| 4,994,085 | 2/1991 | Sawai et al. . |
| 5,015,817 | 5/1991 | Kranz . |
| 5,021,063 | 6/1991 | Tager . |
| 5,047,035 | 9/1991 | Mikhail et al. . |
| 5,047,061 | 9/1991 | Brown . |
| 5,061,287 | 10/1991 | Feiler . |
| 5,078,746 | 1/1992 | Garner . |
| 5,085,548 | 2/1992 | Moyles . |
| 5,108,405 | 4/1992 | Mikhail et al. . |
| 5,116,377 | 5/1992 | Skriptitz et al. . |
| 5,192,282 | 3/1993 | Draenert . |
| 5,192,283 | 3/1993 | Ling et al. . |
| 5,197,841 | 3/1993 | Tanaka . |
| 5,201,769 | 4/1993 | Schutzer . |
| 5,314,489 | 4/1994 | Hoffman et al. . |
| 5,366,441 | 11/1994 | Crawford . |
| 5,443,469 | 8/1995 | Smith . |
| 5,470,336 | 11/1995 | Ling et al. . |
| 5,480,452 | 1/1996 | Hofmann et al. . |
| 5,507,830 | 4/1996 | DeMane et al. . |
| 5,514,135 | 5/1996 | Earle . |
| 5,718,707 | 2/1998 | Mikhail . |

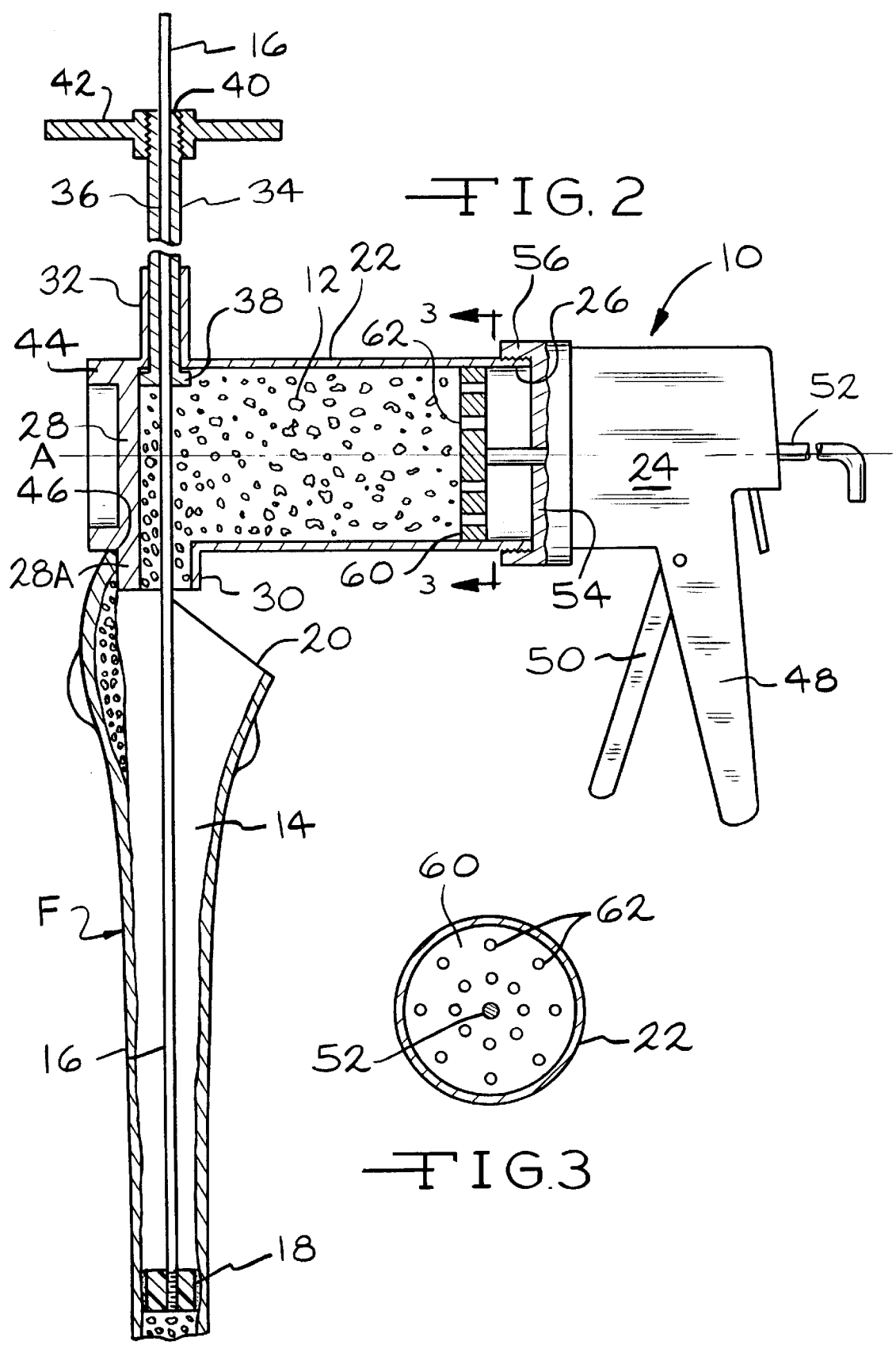

METHOD AND APPARATUS FOR POSITIONING AND COMPACTING BONE GRAFT

CROSS-REFERENCE TO RELATED APPLICATION

This a continuation-in-part of application Ser. No. 08/787,140 filed Jan. 22, 1997, now U.S. Pat. No. 5,718,707.

BACKGROUND OF THE INVENTION

In performing hip prosthesis surgery, it is frequently necessary or desirable to place bone graft material in the intramedullary canal of the femur in order to promote new bone growth. This is particularly true in revision surgery in which a previously implanted femoral prosthesis is removed and replaced with a new prosthesis. The reason for this is that the cavity formed by removal of the previously implanted prosthesis and any old bone cement, particulate debris, membrane, beads and other remnants associated with cemented or cementless femoral prosthesis removal results in a cavity significantly larger than is desired for implantation of a new prosthesis.

In U.S. Pat. Nos. 5,047,035 and 5,108,405, of which I am a co-inventor, a method and apparatus for reaming a cavity in a femur are disclosed. In U.S. Pat. Nos. 5,192,283, 5,470,336 and 5,683,395, of which I am also an inventor or co-inventor, there is disclosed method and apparatus for compacting bone graft material using a cannulated tamp.

Under the parent application to the present continuation-in-part application there was provided a method and apparatus for both dispensing bone graft material directly into a femoral cavity and for at least preliminarily compacting bone graft material in such cavity while utilizing a guide wire to ensure proper positioning.

SUMMARY OF THE INVENTION

Under the present invention there is provided a modified method and apparatus in which the dispenser is provided with an exchangeable modular compaction head so that the head can readily be changed from a relatively smaller head for use in compacting bone graft in the distal end of the prepared cavity to a larger head for use in compacting bone graft material in the larger size cavity closer to the proximal end. The present embodiment also provides for gripping or stabilizing means for supporting the dispensing area of the dispenser on the prepared edge of the bone defining the proximal edge of the cavity. Additionally, the present invention provides for utilization of a multi-piece guide wire which is separable in an area a short distance spaced outwardly from the cut edge of the bone defining the proximal end of the cavity in order to permit removal of the dispenser and its compactor from the cavity and replacement with a cannulated tamp and/or trial prosthesis without the need for removing the distal portion of the guide wire from the prepared cavity.

IN THE DRAWINGS

FIG. 2 is a elevational view partly in section showing the dispenser ready for dispensing bone graft material into a femoral cavity.

FIG. 3 is a sectional view taken along line 3—3 of FIG. 2.

BEST MODE OF CARRYING OUT INVENTION

Figure 1:
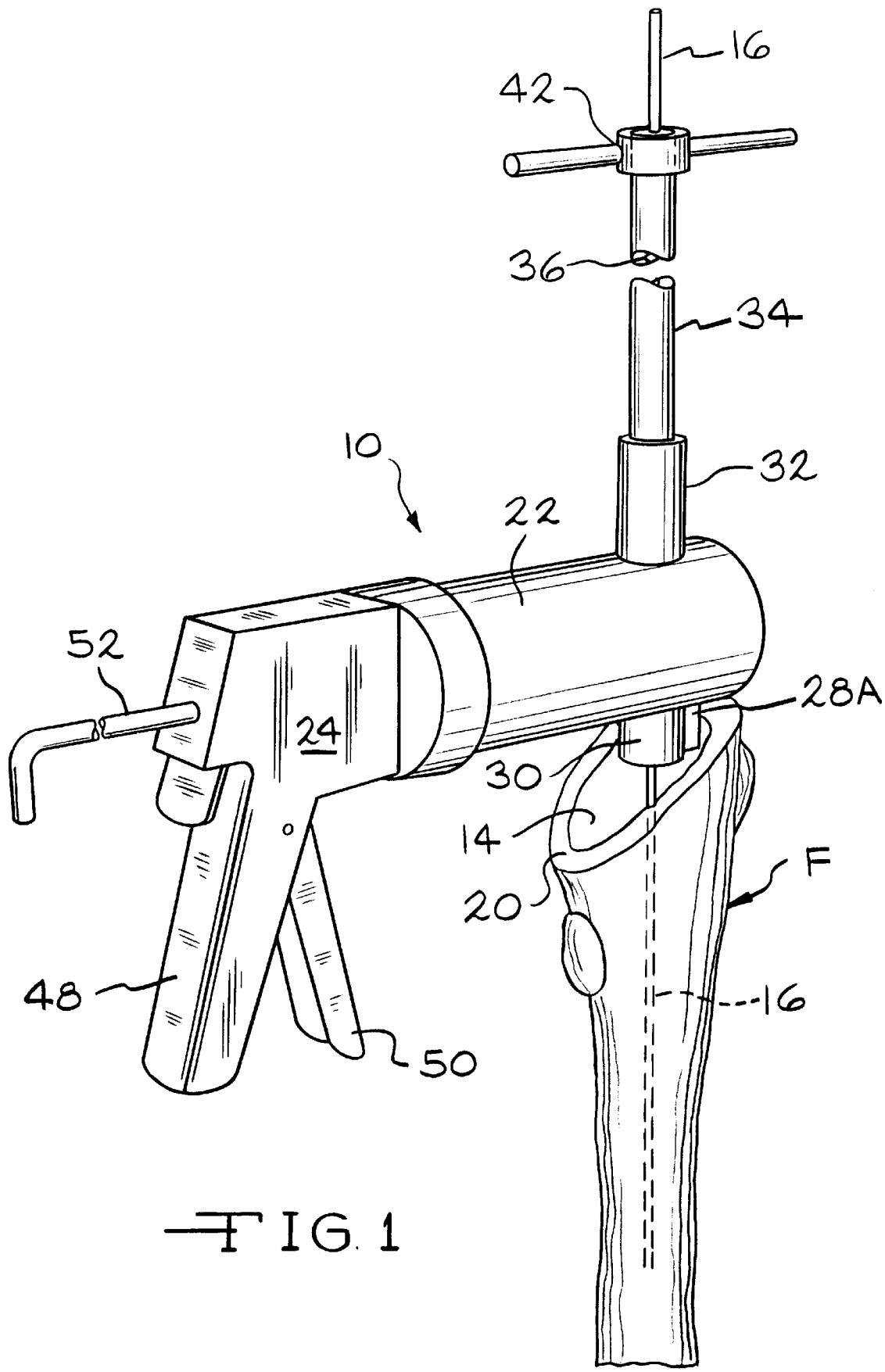
FIG. 1 is a perspective view showing one embodiment of the dispenser of the present invention aligned with the proximal end of a cut femur having an enlarged cavity into which bone graft material is to be dispensed.

Referring now to FIGS. 1 through 3, there is shown a dispenser 10 for introducing bone graft material 12 into a cavity 14 of a femur F. The cavity 14 as shown in FIGS. 1 and 2 is significantly larger than the prosthesis intended to be implanted therein. Such enlarged cavity may result from the fact that the patient previously had another femoral prosthesis implanted in the femur F which failed or was otherwise required to be removed. In removing the previously implanted prosthesis in revision surgery, it is necessary to remove not only the failed prosthesis but also any bone cement utilized therewith or debris of a cementless prosthesis. The cavity 14 may be prepared according to the teachings of my prior U.S. Pat. Nos. 5,047,035 and 5,108,405 in which a reamer is utilized in combination with a guide wire in order to ensure proper alignment of the cavity 14.

As shown in FIG. 2, a guide wire 16 is threadedly engaged to a plug or cement restrictor 18 positioned in the distal end of the cavity. The guide wire extends out of the proximal end 20 of the cavity 14 to a position extending beyond such proximal end a distance sufficiently far for the dispenser 10 to be positioned thereover, a distance, for example, of 15 to 25 cm.

The dispenser 10 as shown in FIGS. 1 and 2, includes a barrel 22 and an actuator 24 secured thereto, for example by threaded engagement.

The barrel 22 includes a cylindrical wall extending from a receiving end 26, to which the actuator 24 is removably engaged, to an end wall 28. Extending downwardly (as viewed in FIGS. 1 and 2) at substantially right angles to the axis A of the cylindrical wall of the barrel 22 is a dispensing nozzle 30. As can be seen in FIG. 2, the dispensing nozzle 30 is adjacent end wall 28 and an extension 28A of such end wall 28 forms a portion of the dispensing nozzle 30. Extending upwardly (as viewed in FIGS. 1 and 2), in alignment with the dispensing nozzle 30, is a tubular section 32.

Figure 4:
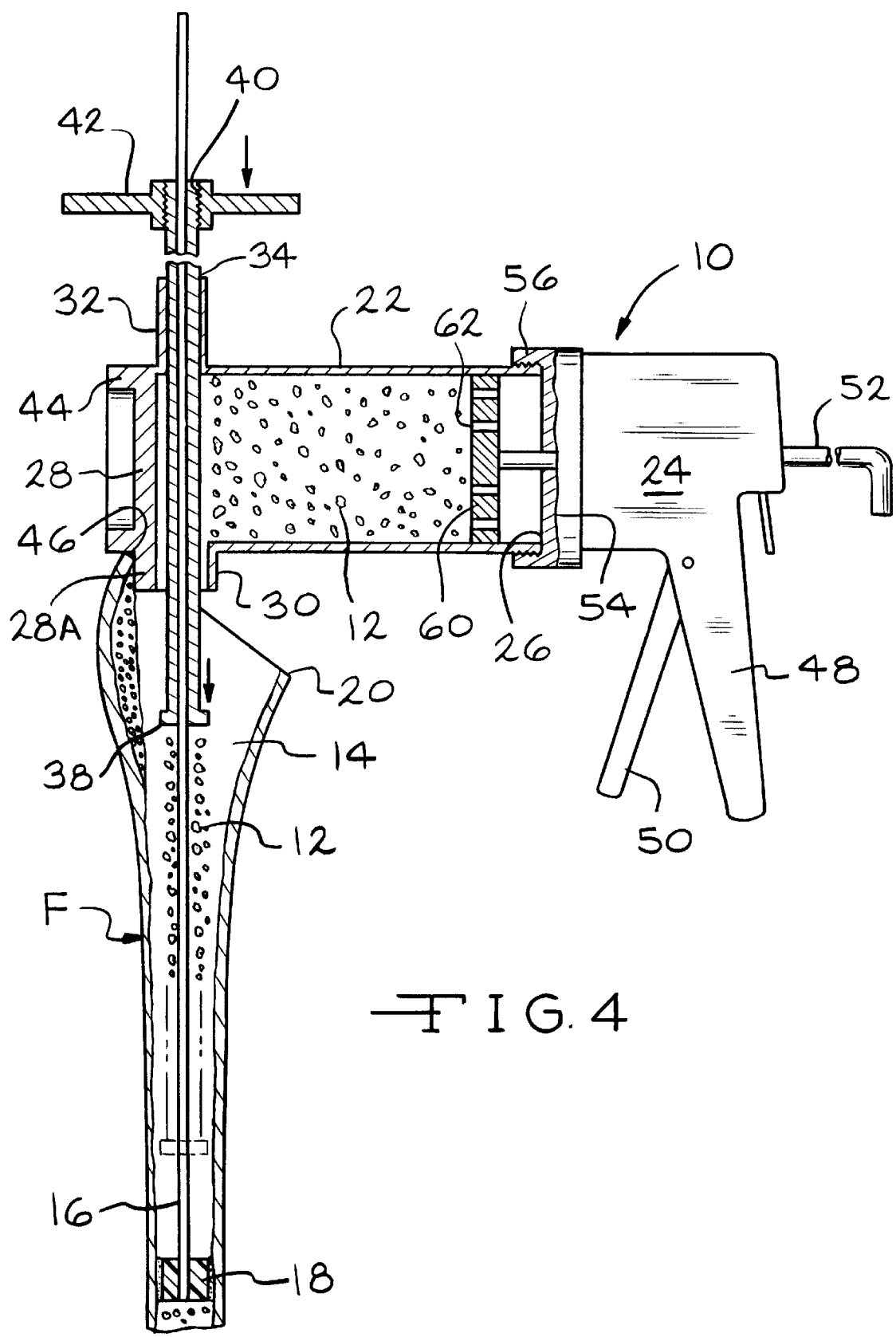
FIG. 4 is a view similar to FIG. 2 showing ejection of bone graft material from the dispenser and into the cavity and showing in dashed lines extension of the plunger to a position for compacting.
Figure 5:
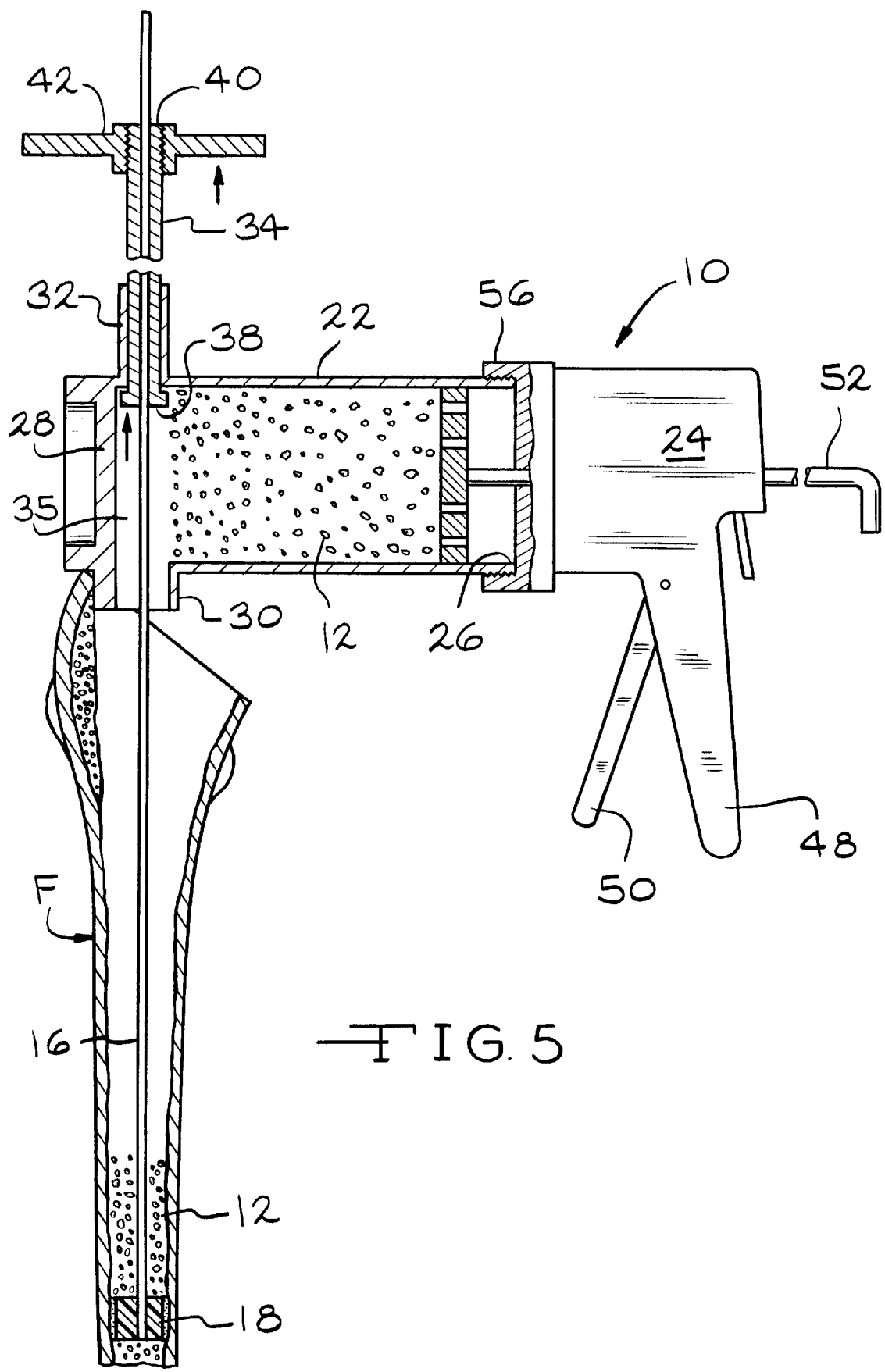
FIG. 5 is a view showing retraction of the ejector member preparatory to dispensing another quantity of bone graft material into the cavity.

Mounted in sliding engagement with the interior surface of the tubular section 32 is a cannulated ejector member 34 having a central passageway 36 sized to receive the guide wire 16 and to slideably move relative to such guide wire 16. The ejector member 34 has an enlarged head 38 which is sized smaller than the interior wall of tubular section 32 to prevent withdrawal of the head 38 through such tubular section 32 thereby preventing disassociation of the ejector member 34 from the barrel 22. The enlarged head 38 is slightly smaller than the interior surface of the dispensing nozzle 30 so that it may readily slide therethrough as shown by comparing FIG. 2 with FIG. 4. The tubular section 32 extends upwardly to a threaded or locking end portion 40 to which may be engaged a T-bar 42 having a threaded collar engaged to the locking threaded end 40. The T-bar 42 may be used for manually sliding the ejector member 34 from the raised or retracted position shown in FIG. 2 to the lowered or extended position shown in FIG. 4. If desired, the T-bar could be an integral part of the ejector member.

Extending along the axis A from the end wall 28 is a short cylindrical section 44, the lower portion of which cooperates with end wall extension 28A to define a corner support 46 which may rest upon the proximal end 20 of the prepared femur, preferably along the lateral side to stabilize the dispenser 10.

The actuator 24 includes a handle 48 and a pivotally mounted trigger 50 attached to a rachet-type push bar 52 such as those commonly used with caulking guns. The push bar 52 extends through the end wall 54 of a collar member 56 which is threadedly engaged or locked to the receiving end 26 of the barrel 22. Supported on the end of the push bar 52 is a plunger 60 sized to be slidably engaged with the interior surface of the barrel 22. The plunger 60 has a plurality of apertures 62 formed therein for permitting the escape of any liquid material such as marrow, fat and blood which may have accumulated in the bone graft 12.

In operation, bone graft 12 is inserted in the barrel 22 and the actuator 24 is threadedly or lockingly engaged to the barrel 22 with the plunger 60 in the retracted position shown in FIG. 2. Preferably, the ejector member 34 will be in its raised position upon the introduction of bone graft 12 into the barrel 22 and engagement of the actuator 24 thereto. The dispenser 10 thus loaded is positioned over the guide wire 16, with the guide wire 16 extending through the passageway 36 of the ejector member. Preferably, the dispenser 10 is supported at the proximal end 20 of the femur F with the corner support 46 engaging such proximal end 20 at the lateral cortex. With the dispenser 10 thus positioned, the ejector member 34 is pushed downwardly by manual gripping or hammering on the T-bar 42 so that the enlarged head 38 pushes bone graft material out of the dispensing nozzle 30 and into the cavity 14. Preferably, the ejector member 34 has sufficient length such that the head 38 can compact the bone graft 12 substantially completely to the restrictor 18 as shown in phantom lines in FIG. 4.

Figure 6:
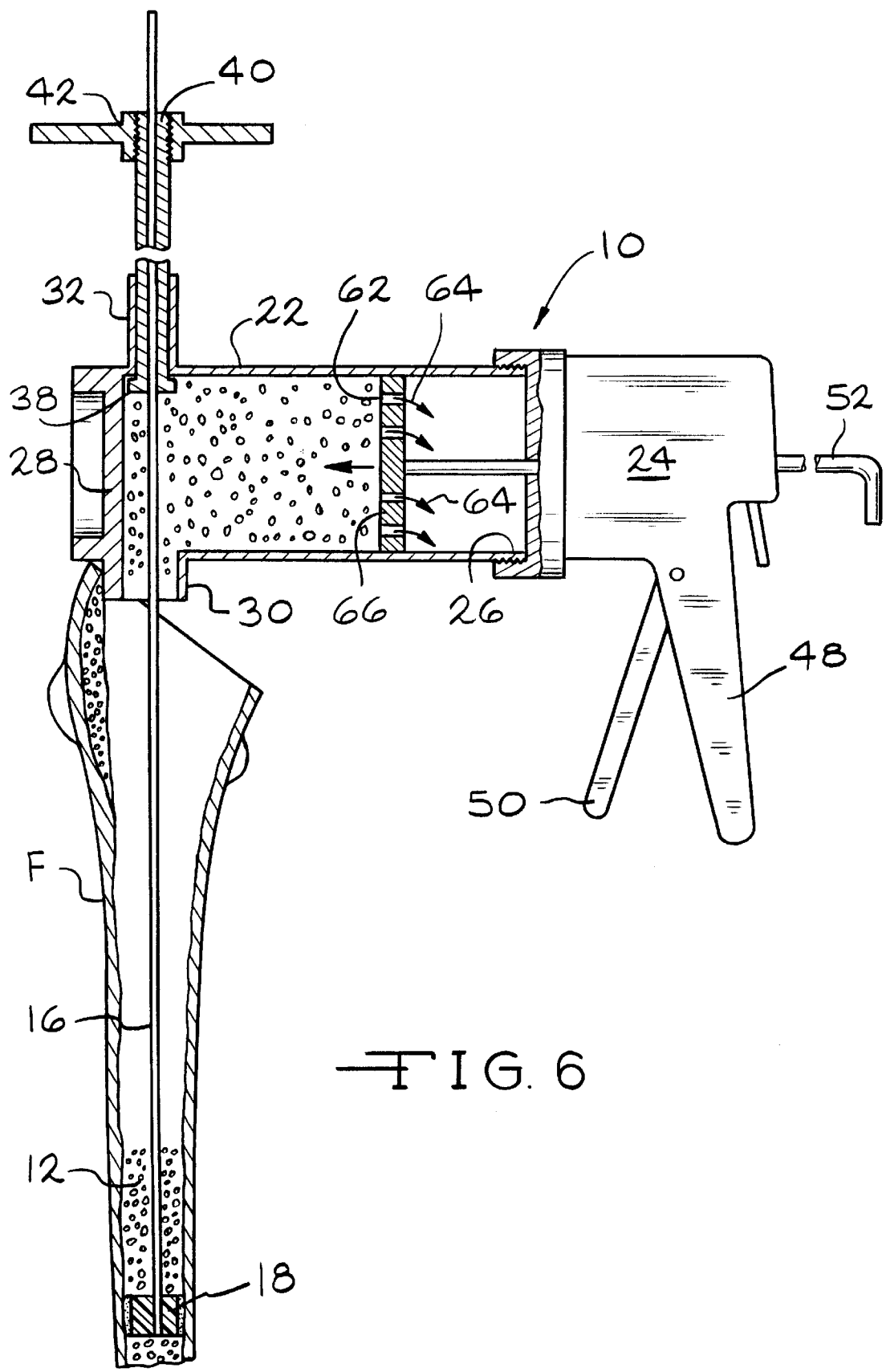
FIG. 6 is a view similar to FIG. 5 showing movement of the plunger to push the bone graft material into alignment with the dispensing ejector member.

The ejector member 34 is then raised to the position shown in FIG. leaving a space 35 from which the bone graft 12 was ejected. The trigger 50 is then actuated to force the plunger 60 further into the barrel 22 causing bone graft 12 to fill the space 35 with the portion adjacent the wall 28 being aligned with the dispensing nozzle 30 and the enlarged head 38 ready for ejection upon lowering of the ejector member 34. As shown in FIG. 6, as the plunger moves toward the end wall 28 to move bone graft material 12 into position for ejection by the ejector member 34 and compressing such bone graft, undesirable liquids shown by arrows 64 in FIG. 6, may seep through the apertures 62.

Figure 7:
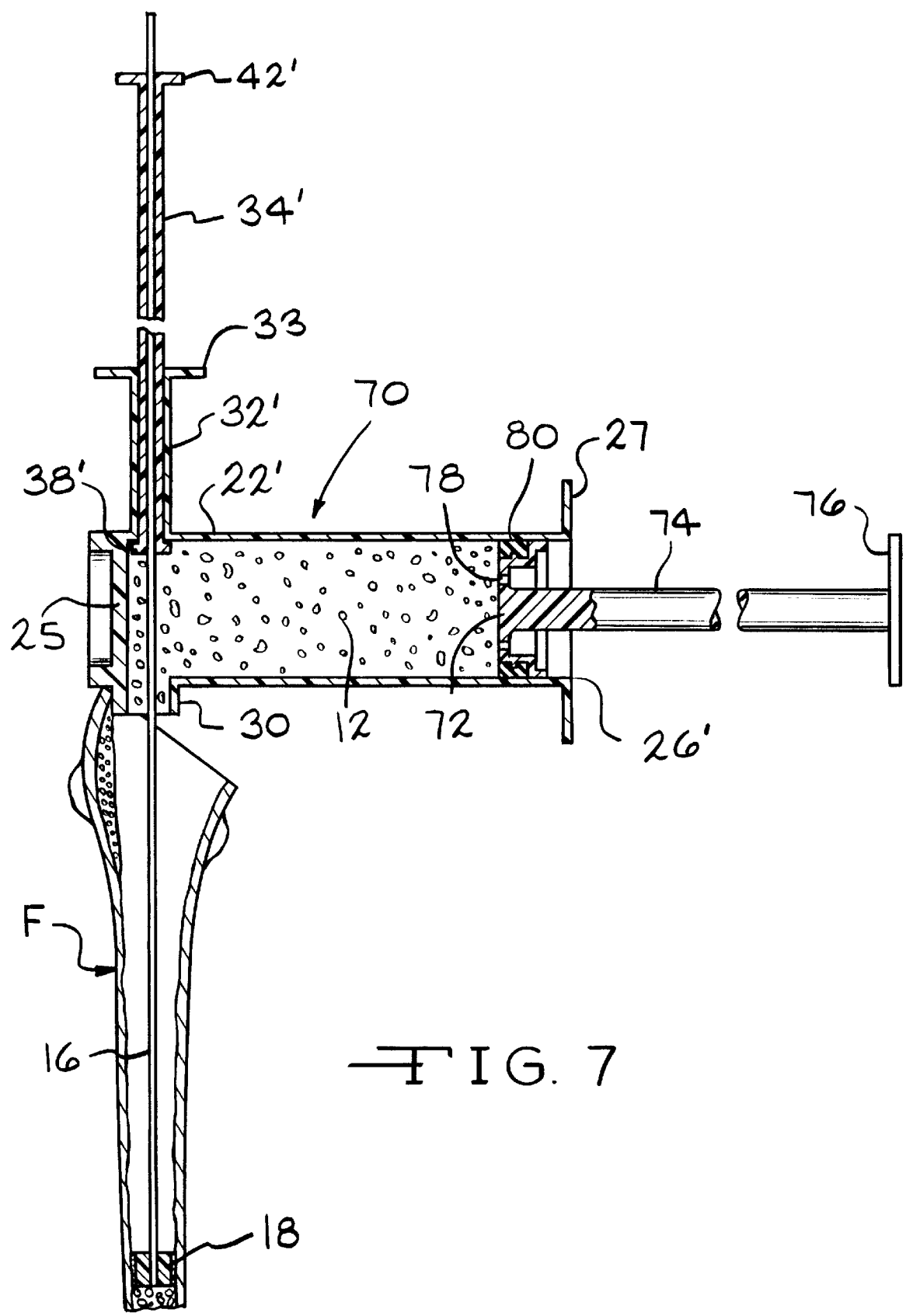
FIG. 7 is an elevational sectional view of a modified dispenser.

Referring now to FIG. 7, there is shown a modified dispenser 70 which is similar to the dispenser 10 except that, in place of having an actuator 24 threadedly engaged to the barrel 22, there is provided a plunger 72 which is moveable manually by a push bar 74 having an enlarged head 76. The plunger 72, push bar 74 and enlarged head 76 may be a desired medical grade plastic material and molded as a single, unitary article. As with the previous embodiment, the plunger 72 has a plurality of apertures 78 through which undesirable liquid material may be expelled from the bone graft material as the push bar 74 pushes the plunger 72 toward the end wall 28. The plunger 72 includes an annular groove in which is positioned an O-ring 80 which is slidingly and sealingly engaged to the interior wall of the barrel 22'. If desired, the barrel 22' may be provided with a radial flange 27 at its receiving end 26' to provide rigidity necessary to maintain the receiving end with a constant cross sectional configuration to snugly receive the plunger 72. The barrel 22' and all elements integral therewith (i.e. flange 27, end wall 28, dispensing nozzle 30, tubular section 32' with its flange 33) may also be formed of a suitable plastic such as polyethylene.

The ejector member 34' and integral T-bar 42' and enlarged head 38' may also be formed of plastic. When formed of plastic material, the dispenser 70 is sufficiently economical to be disposed of after a single use.

Figures 8, 9:
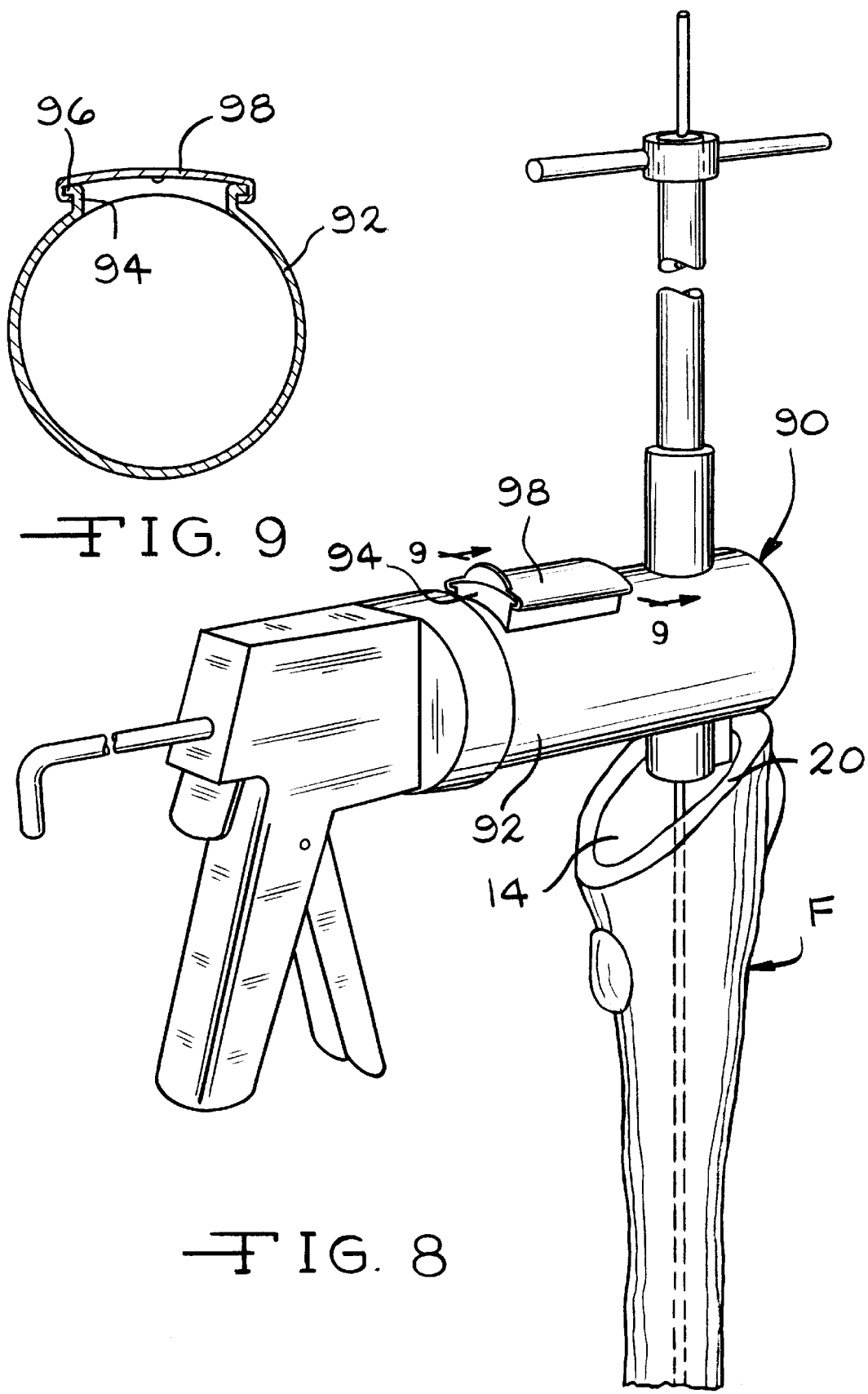
FIG. 8 is perspective view showing a further modified dispenser.
FIG. 9 is a sectional taken through 9—9 of FIG. 8.

Referring now FIGS. 8 and 9, there is shown a dispenser 90 which is similar to the dispenser 10 of the embodiment of FIGS. 1 through 6 with the exception that it is provided with access means to the interior of the barrel 92. As can be seen in FIGS. 8 and 9, the barrel has a rectangular wall 94 extending upwardly therefrom. A pair of parallel outwardly extending flanges 96 extend from two of the walls 94. Slideably engaged to the flanges 96 is a cover 98 which may be easily opened to introduce bone graft material into the barrel 92 without the necessity of removing the actuator 24.

Referring now to FIGS. 10 through 13, there is provided a modified dispenser 110 having a barrel 122 in combination with the actuator 24 of the type previously described with respect to FIGS. 1 through 6. The barrel 122 includes a cylindrical wall extending along an axis A from a receiving end 126 to which the actuator 24 is removably engaged to an end wall 128. A dispensing opening 130 is provided adjacent the end wall 128. Extending downwardly as viewed in FIG. 10 (upwardly as viewed in FIG. 13) from the barrel 122 are (1) an inner bone engagement member 133 aligned with that portion of the opening 130 adjacent end wall 128 and (2) an outer bone engagement member 134 spaced therefrom a distance sufficient to permit the spaced apart inner engagement member 133 to fit inside the bone cavity and the outer engagement member 134 to be positioned on the outside of the bone with the juncture 136 between the inner engagement member 133 and outer engagement member 134 resting upon the proximal end 20 of the prepared bone. The outer engagement member 134 has a gripping surface, preferably with serrations 143 facing the inner engagement member 133 which preferably is disposed at an angle to the inner engagement member 133 so that the space between such members increases in size in a direction away from the juncture 136. On the opposite side of the opening 30 from the inner engagement member 133 is a shield 138 extending downwardly (as viewed in FIG. 10) from the barrel 122 a distance sufficient to be positioned within the cavity 14 to direct the flow of bone graft material 12 into the cavity. The shield 138 preferably has an arcuate cross-sectional configuration extending at least 90° around the periphery of the opening 130. Extending upwardly (as viewed in FIG. 10) from the portion of the barrel 122 opposite the opening 130 is a tubular section 132.

Mounted in sliding engagement with the interior surface of the tubular section 132 is a cannulated ejector/compactor member 135 having a central passageway 137 sized to receive the guide wire 116 and to slideably move relative to such guide wire 116. The ejector/compactor member 135 has a modular head 140 which is removably secured to the ejector/compactor member 135 by a threaded or locking stem portion 141 engaging an internally threaded portion 139 of the distal end of the ejector/compactor member 135. Additionally, the ejector/compactor member 135 is provided with calibrations in millimeters and centimeters in order to permit the surgeon to determine the varying depth of the cavity 14 as the bone graft material is introduced and compacted therein. As may be seen particularly in FIGS. 10, 11 and 13, the ejector/compactor member 135 may have engaged thereto a handle 145 and enlarged ears 146 which are suitable for gripping and striking with a hammer for effecting compaction force to the head 140.

Figure 10:
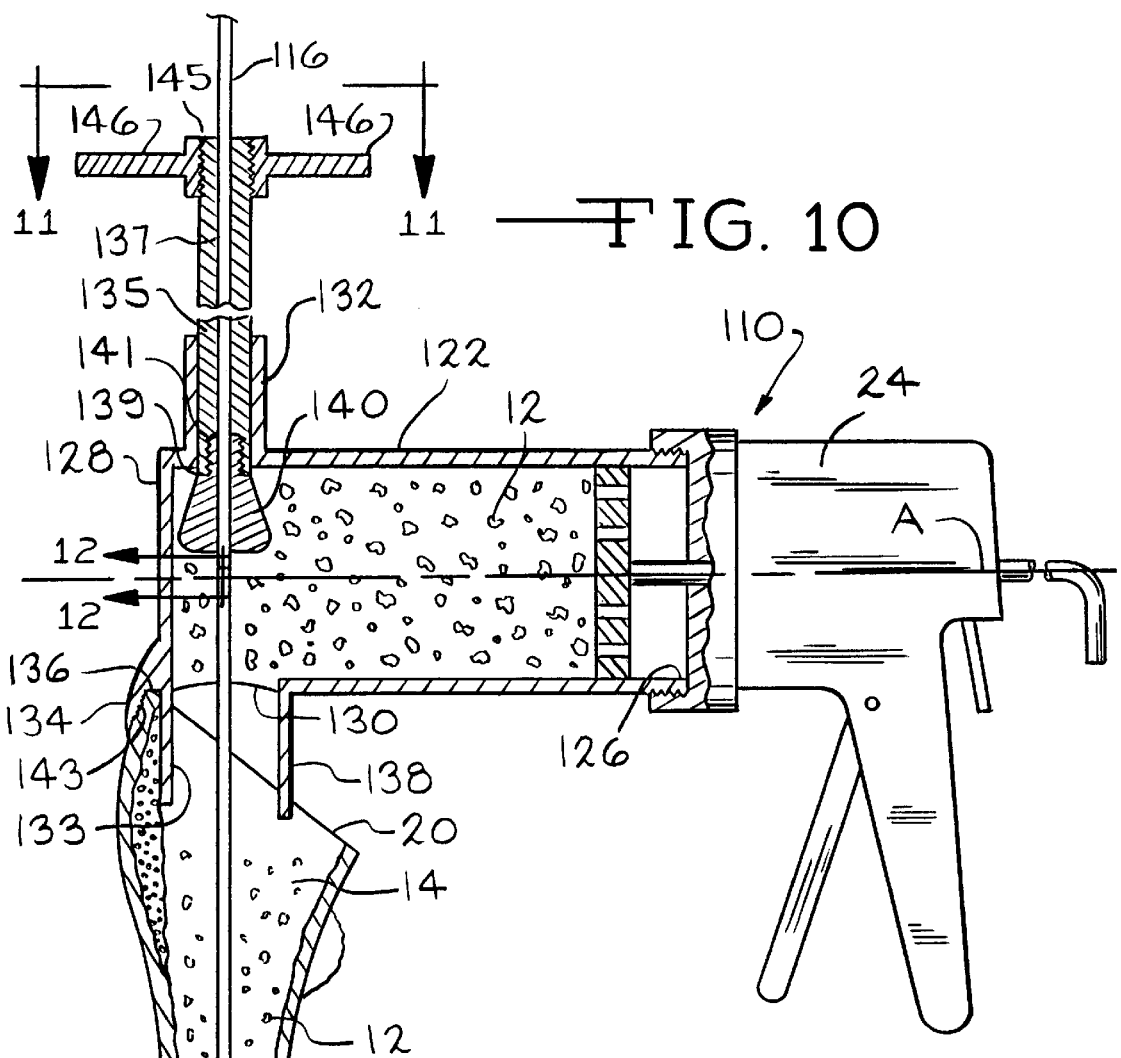
FIG. 10 is a view similar to FIG. 2 showing a modified embodiment.
Figure 11:
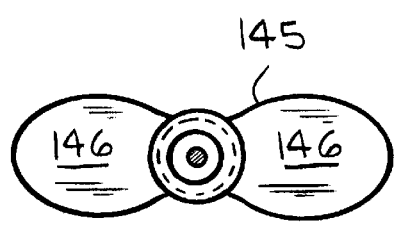
FIG. 11 is a view taken along line 11—11 of FIG. 10 showing one configuration of handle for the ejector/compactor member.
Figure 12:
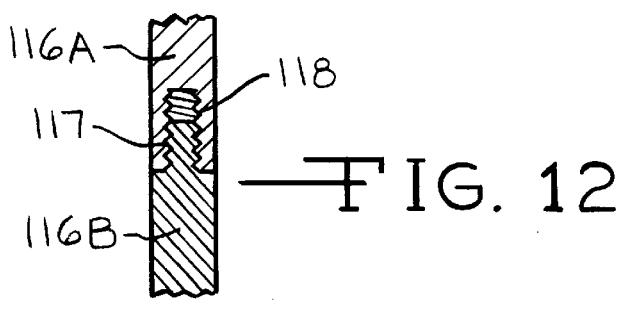
FIG. 12 is a sectional view through the guide rod taken along line 12—12.
Figure 13:
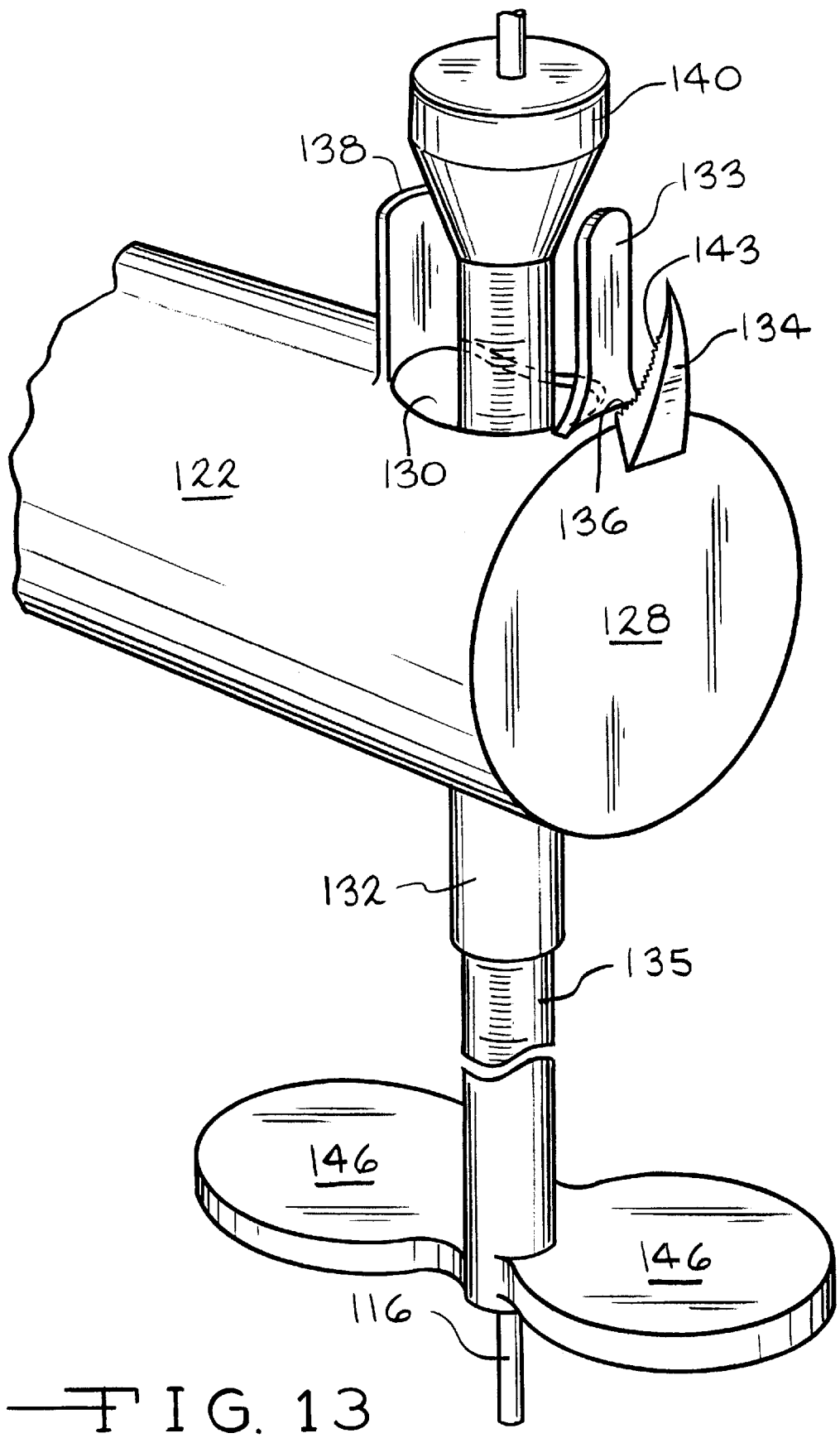
FIG. 13 is a perspective view showing the dispenser of FIG. 10 in an inverted position.
Figure 19:
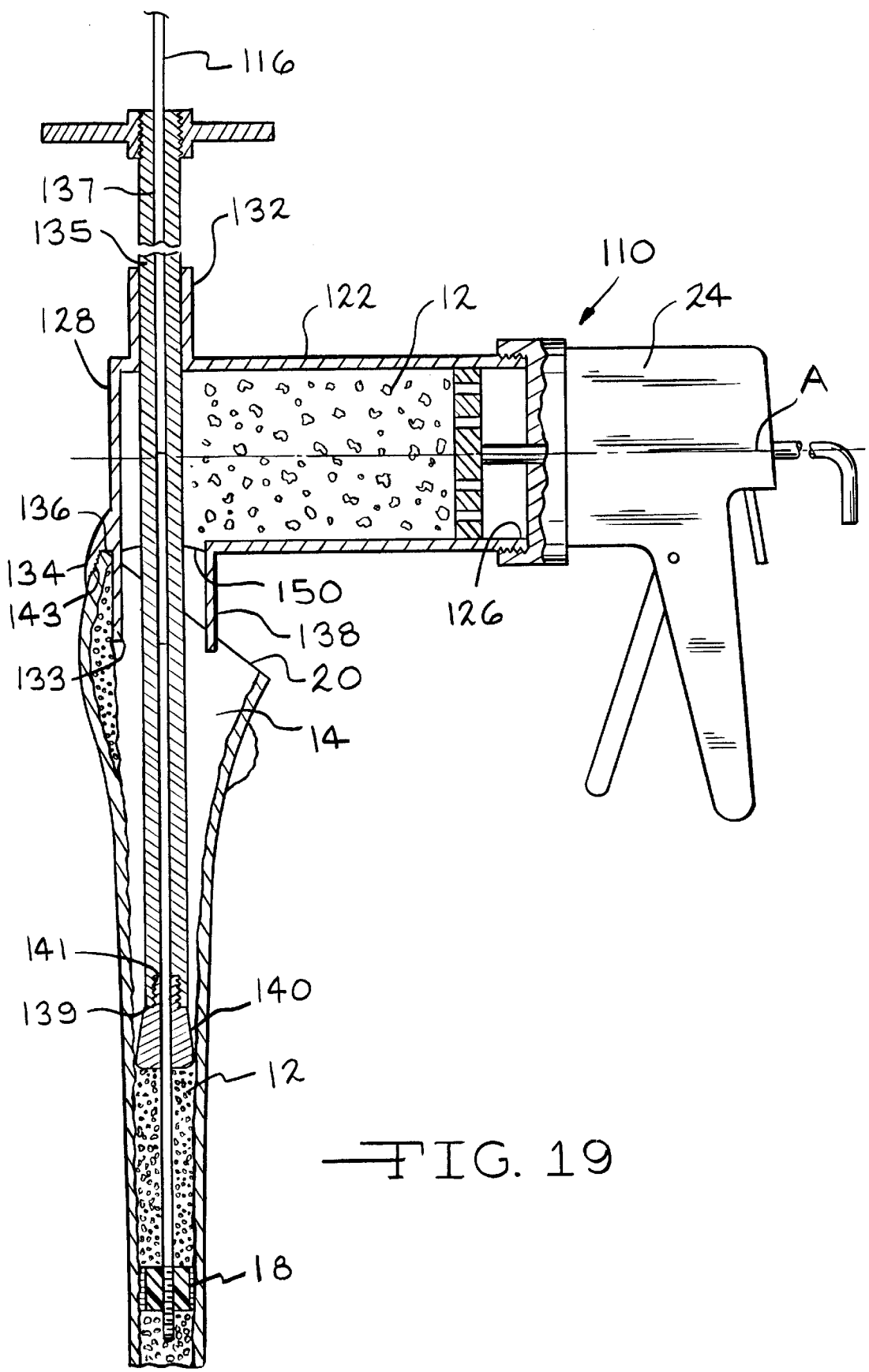
FIG. 19 is a view similar to FIG. 10 showing the compaction head compacting bone graft material near the distal end of the cavity.

In FIG. 10, the ejector/compactor member 135 is in its most retracted position with the modular head 140 located within the barrel 122 and ready to be moved to an extended position shown in FIG. 19. As the head 140 moves through the barrel 122 at right angles to the axis A and along the axis defined by the guide wire 116, it will eject bone graft material 12 out of the opening 130 and into the cavity 14 where continued movement toward the distal end will cause the head 140 to compact the bone graft material 12 positioned between the head and the plug 18. As can be seen from FIGS. 10 and 19, the end of the dispenser 110 adjacent end wall 128 is supported on the cut edge 20 of the bone with the bone fitting between the inner engagement member 133 and the serrations 143 of the outer engagement member 134 and with the juncture 136 resting upon the cut edge 20. The opposite end of the dispenser 110 is supported by the surgeon gripping the actuator 24.

As can be seen from viewing FIGS. 10 and 19, the cavity 14 increases in cross-sectional size as it approaches the proximal end 20. When the level of the compacted bone graft material 12 reaches a level toward the proximal end 20 with an enlarged cross-sectional size, the modular head 140 of the ejector/compactor member 135 may be removed by unthreading or unlocking and replaced with a new modular head having a larger surface area at the compacting end facing the distal end of the cavity 14.

Figure 14:
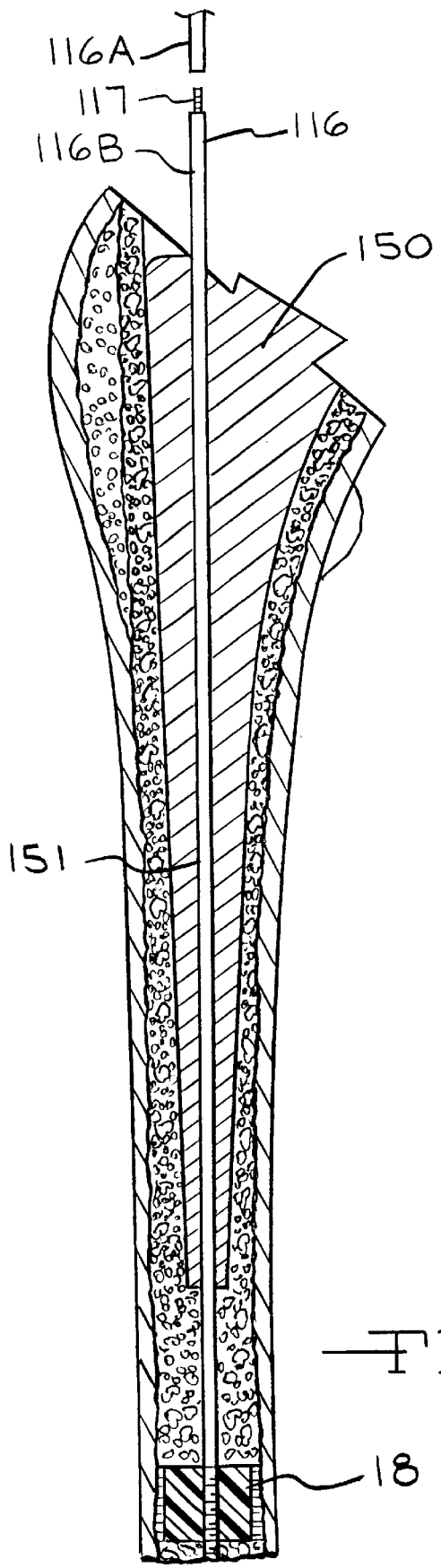
FIG. 14 is a sectional view showing a prepared cavity with compacted bone graft material and a cannulated tamp telescoped over the separated guide rod.

As can be seen in FIG. 14 and as described in my previously identified Patent Nos. 5,192,283 and 5,470,336, it is frequently desired to further prepare the cavity by use of a tamp 150 having a central passageway or cannulation 151. In order to readily position the cannulated tamp 150 over the guide wire 116 and use the tamp 150 as a trial prosthesis without removing the guide wire from the plug 18, it is desired that the guide wire 116 be formed in two sections, namely, a proximal section 116A and a distal section 116B. The proximal section 116A may be joined to the distal section 116B by any preferred means, for example by a threaded stem 117 extending from the distal section 116B being threadedly engaged to inwardly facing threads 118 of the proximal section 116A as shown in detail in FIG. 12. This is desirable because the preferred length of the overall guide wire 116 when used with the dispenser 110 is so long that the proximal end of a unitary guide wire would interfere with the use of the cannulated tamp 150 thereover as a trial prosthesis in order to determine the stability and the appropriate size of the final or actual implantable femoral component or prothesis. By removing the proximal section 116A when the surgeon is finished using the dispenser 110 and its ejector/compactor 135, the dispenser 110 may be readily removed and the cannulated tamp 150 may be readily positioned over the distal section 116B without removing it from the plug 18. It is not desirable to remove the distal section 116B from the plug 18 prior to positioning the cannulated tamp 150 thereover as removal of the guide wire for trial reduction then reinsertion of the wire may lead to tilting or malalignment of the prosthesis. After completion of use of the cannulated tamp 150 as a trial prosthesis, the distal section 116B of the guide wire may be removed. The femur is then ready to receive the prosthesis and any bone cement intended to be used therewith.

Figure 15:
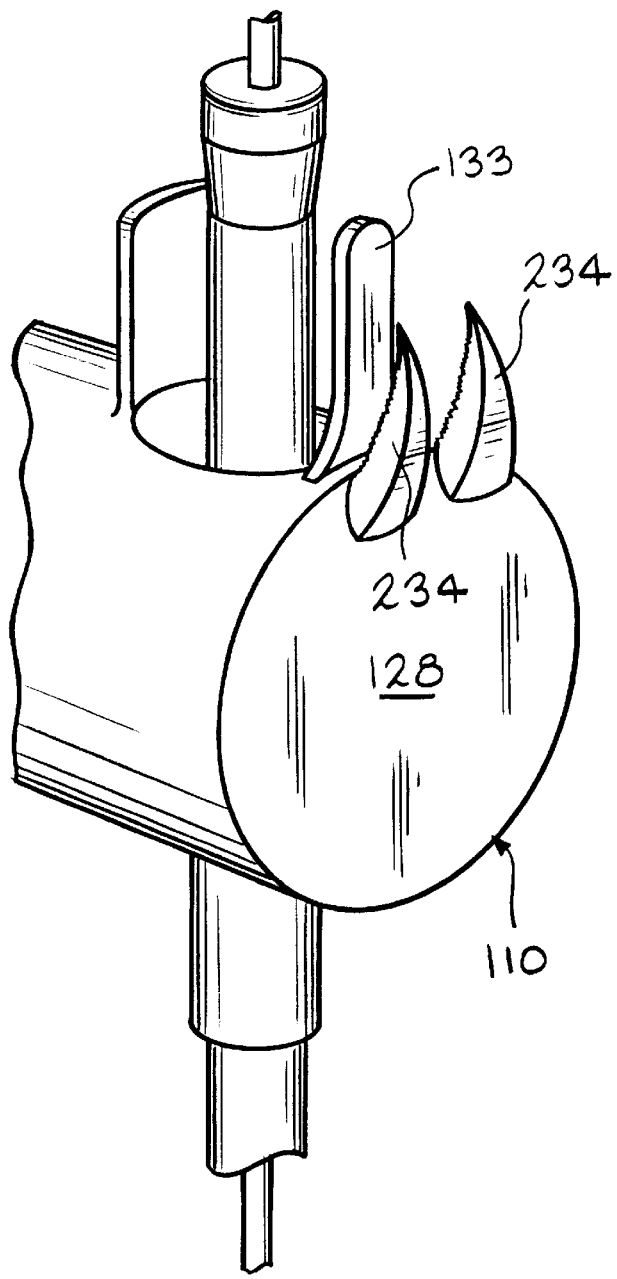
FIG. 15 is a fragmentary perspective view of another embodiment of dispenser.

Referring to FIG. 15, there is shown a modification in which the dispenser 110 is provided with a pair of outer support members 234 extending outwardly from the end wall 128 in spaced relationship with a inner support member 133.

Figure 16:
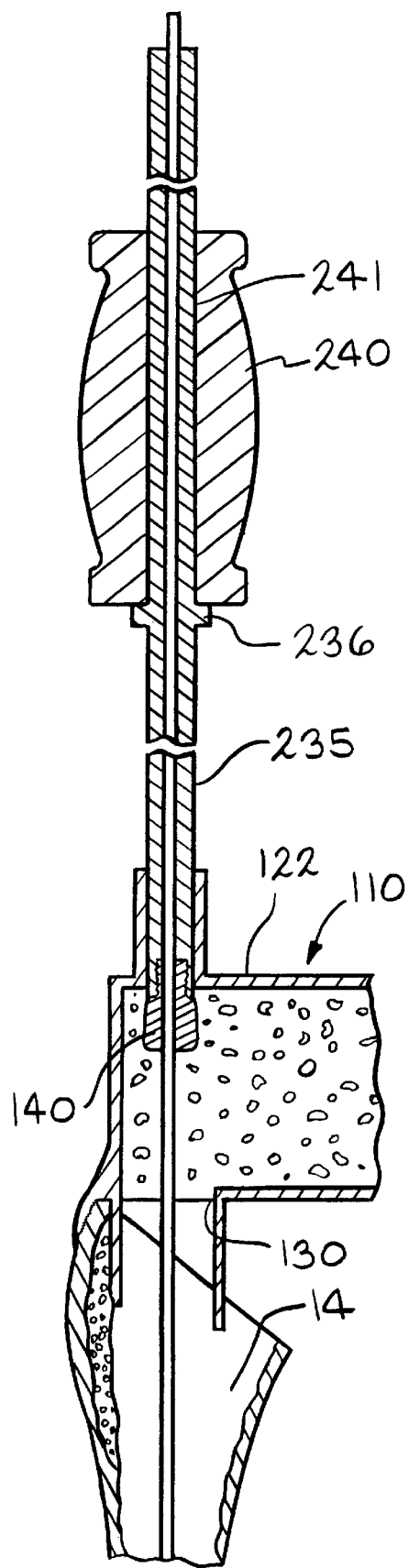
FIG. 16 is a fragmentary sectional view of another embodiment having a slap hammer to assist in compacting bone graft material.

FIG. 16 shows a further modified embodiment in which the dispenser 110 is provided with an ejector member 235 having a radially outwardly extending flange 236 positioned in an area which will be located at all times on the opposite side of the barrel 122 from the opening 130, even when the head 140 is at its lowermost position compacting bone graft material at the distal end of the cavity 14. A slap hammer 240 having a central passageway 241 sized to slidingly receive the ejector member 235 is telescoped over the ejector member on the opposite side of the flange 236 from the barrel 122. The slap hammer 240 can be raised away from the flange 236 and impacted thereagainst in order to assist the head 140 in compacting the bone graft material 12 being introduced into the cavity 14. If desired, the slap hammer 240 may have a longitudinal slot extending throughout with a breadth slightly greater than the diameter of the ejector member 135 so that the slap hammer can be positioned thereon for impaction simply by moving it laterally to the axis of the ejector member rather than telescoping it over the end of the ejector member 235 as is required with an ejector member having a full circumferential extent.

Figure 17:
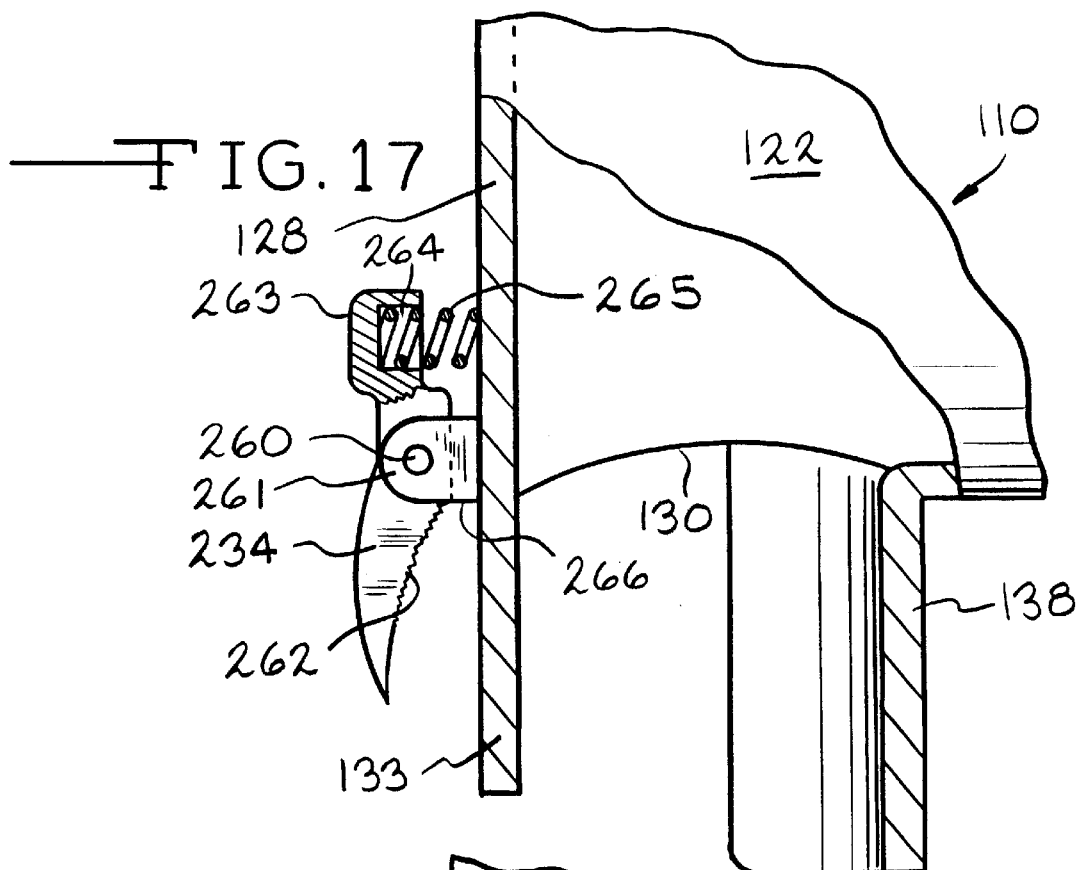
FIG. 17 is a fragmentary view showing a feature for stabilizing the dispenser on the prepared cut edge of the femur intended to receive the bone graft material.

Referring to FIG. 17, there is provided a further embodiment in which means are provided for actually gripping the bone to assist in supporting the dispenser 110 while dispensing bone graft material. In the embodiment of FIG. 17, the barrel 122 is still provided with an opening 130 adjacent the end wall 128 and the inner support member 133 and shield 138 as described with respect to the embodiment of FIG. 10. There is also provided an outer support member 234 pivotally mounted by a pin 260 on a bracket 261 secured to the end wall 128. The outer support member 234 includes a lower portion (as viewed in FIG. 17) having serrations 262 for gripping the bone disposed in spaced relationship with the inner support member 133 intended to engage the inner surface of the bone facing the cavity. The outer support member 234 has an enlarged head 263 with a cavity 264 facing the end wall 128. Positioned in and extending outwardly from the cavity 264 is a compression spring 265 which yieldingly urges the head 263 away from the end wall 128. As a result of the action of the compression spring 265 and the mounting of the outer support member 234 on the pivot pin 260, the portion of the outer support member with the serrations 262 will be urged into gripping engagement with the outer surface of the bone upon which it is supported. As will be appreciated, the lower portion 266 of the bracket 261 in the area between the serrations 262 and the inner support member 133 will rest upon the cut edge of the bone. After the bone graft material has been introduced and compacted, the dispenser 110 may be easily removed from the bone simply by pressing the head 263 toward the end wall 128 against the urging of the compression spring 265 to open the gap between the serrations 262 and the inner support member 133.

Figure 18:
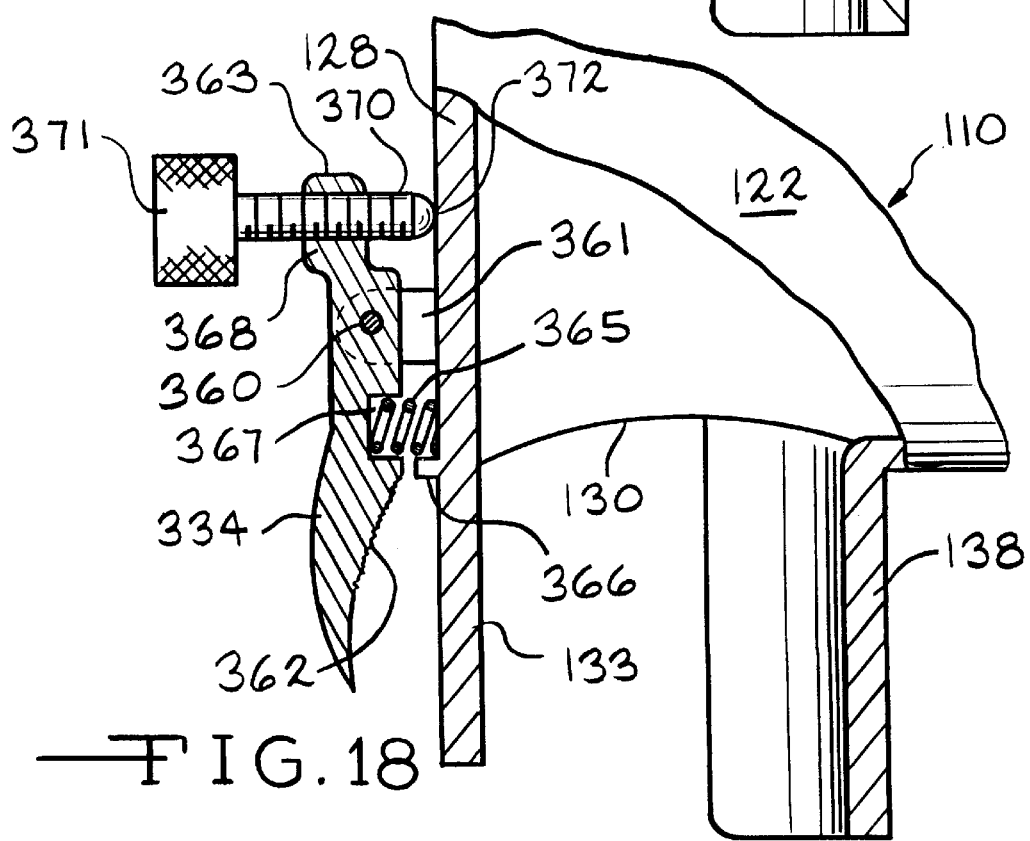
FIG. 18 is a view similar to FIG. 17 showing a modified stabilizing feature.

Referring to FIG. 18, there is provided a further embodiment under which the dispenser 110 may be more positively gripped to the bone edge being engaged. Under this embodiment, there is provided an outer support member 334 which is pivotally mounted on a bracket 361 by a pin 360. Under this embodiment, the bracket 361 is spaced upwardly (as viewed in FIG. 18) from the lowermost portion of the barrel 122 at the opening 130. A guide flange 366 extends outwardly a short distance from the end wall 128 at the lowermost portion of the barrel 122 in the area of the opening 130. As in the previous embodiment, the outer support member 334 has serrations 362 but which, in this embodiment, are positioned below the flange 366.

In the area immediately above the flange 366, the outer support member 334 is provided with a cavity 367 facing the end wall 128. A compression spring 365 is positioned in the cavity 367 and bears against the end wall 128 to yieldingly urge the portion of the outer support member 334 having the serrations 362 away from the inner support member 133. The portion of the outer support member 334 on the opposite side of the pin 360 has a head 363 with a threaded passageway 368 in which is positioned a threaded thumb screw 370 having an enlarged head 371 which may be readily gripped for rotating the screw 370 in the threaded passageway 368. The screw 370 has an opposing end 372 which engages the end wall 128. As will be appreciated, when it is desired to position the dispenser 110 on the bone or remove it from the bone, the screw 370 will be rotated in a direction causing it to move to the left thereby permitting the compression spring 365 to cause the outer support member 334 to pivot clockwise a short distance about the pin 360 to enlarge the space between the serrations 362 and the inner support member 133. When the dispenser 110 has been properly positioned on the bone for dispensing bone graft material 12 in the cavity 14, the screw 371 may be rotated in the opposite direction to thereby cause the space between the opposing end 372 bearing against end wall 128 and the head 363 to increase and the space between the serrations 362 and the inner support member 133 to decrease to a point where the bone is firmly gripped between the serrations 362 and the inner support member 133.

Figure 20:
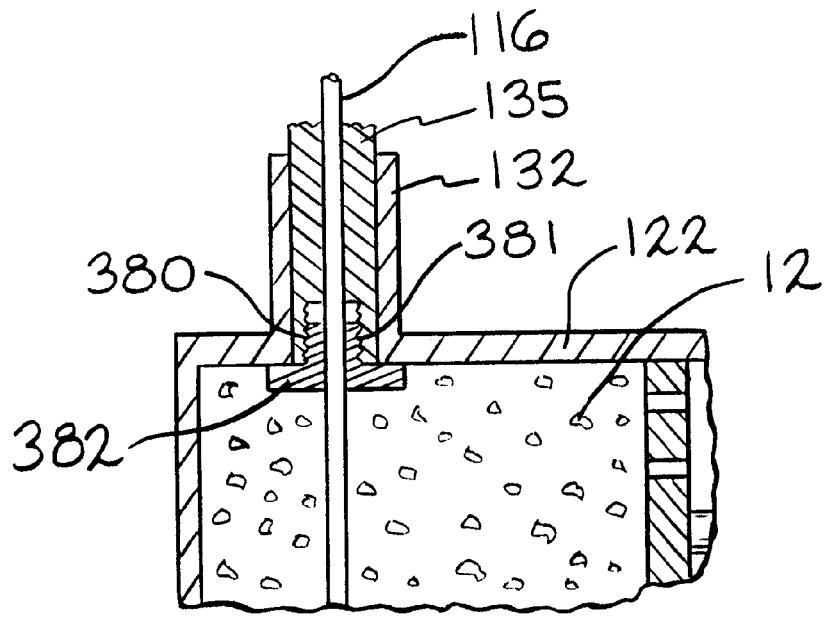
FIGS. 20 and 21 are fragmentary sectional views of further embodiments of dispenser.

Referring to FIG. 20, there is provided a further modification in which the ejector/compactor member 135 is provided with a modular head 380 which is removably secured to the ejector/compactor member 135 by a threaded or locking stem portion 381. The modular head 380 has a substantially flat ejector/compactor element 382 integral with the stem portion 381. As can be readily seen in FIG. 20, the lower surface of the ejector/compactor element is very close to the tubular section 132 at the upper side of the barrel 122 so that there will be more space between such lower surface and the dispensing opening 130 at the opposite side of the barrel 122. This will provide a greater amount of bone graft material 12 dispensed through such opening 130 for each extension of the ejector/compactor member 135.

Figure 21:
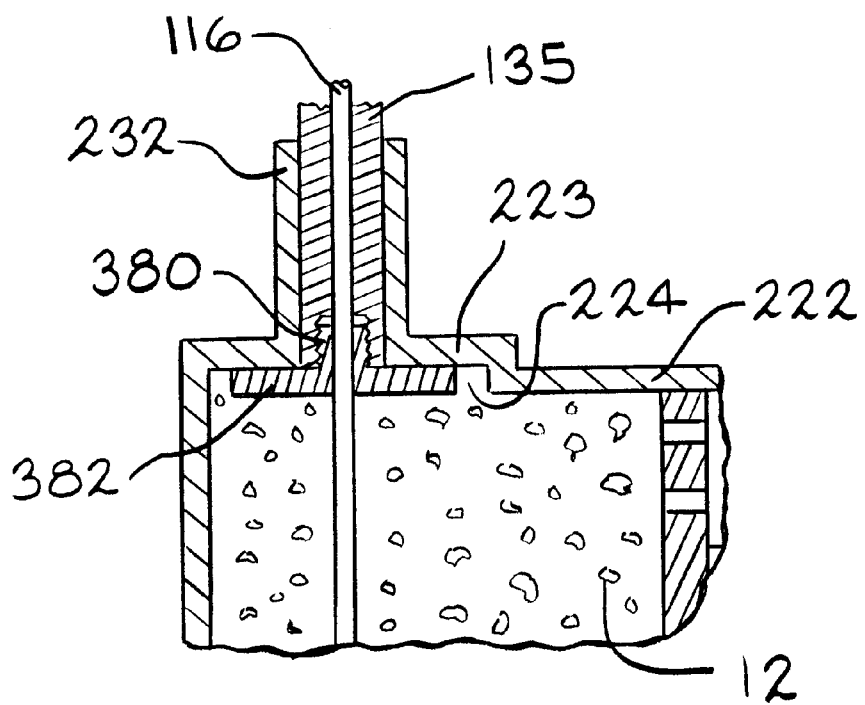

FIG. 21 shows yet another embodiment for maximizing the amount of bone graft material 12 ejected at each extension of the ejector/compactor member 135. Under this embodiment, the dispenser is provided with a barrel 222 having an outwardly protruding area 223 adjacent the tubular section 232 forming a cavity 224 having a depth to receive the ejector/compactor element 382 of the modular head 380. The modular head 380 shown in FIG. 20 has a smaller ejector/compactor element 382 than that shown in FIG. 21 to illustrate the feature of using varying sizes of modular heads.

As used herein, the term bone graft material includes any synthetic or biocompatible substitute material. Other modifications will become readily apparent to those skilled in art. Accordingly, the scope of the claims appended hereto should be determined only by the scope of the claims appended hereto.

I claim:

1. A method for preparing a cavity in a long bone for receiving a prosthesis having an elongated stem comprising:
   (a) forming an enlarged cavity extending from a distal end to a proximal end of said long bone;
   (b) positioning a guide wire in said enlarged cavity, said guide wire extending from said distal end and out of said proximal end;
   (c) positioning a dispenser containing bone graft material on said guide wire, said dispenser including an outlet and an elongated ejector/compactor member extending to a first modular head defining an end having a first size and having a passageway extending therethrough, said guide wire extending through said passageway and said outlet;
   (d) moving said ejector/compactor member on said guide wire toward said outlet and said distal end to eject bone graft material through said outlet and into said enlarged cavity;
   (e) extending said ejector/compactor memberdistally into said enlarged cavity to a position at which said first modular head compacts said ejected bone graft material;
   (f) replacing said first modular head with a second modular head defining an end with a second size different from said first size; and
   (g) positioning additional bone graft material between said second modular head and said outlet and moving said ejector/compactor member toward said distal end to cause said second modular head end to expel additional bone graft material through said outlet and into said enlarged cavity and compact said bone graft material.

2. A method for preparing a cavity in a long bone for receiving a prosthesis having an elongated stem comprising:
   (a) forming an enlarged cavity extending from a distal end to a proximal end of said long bone;
   (b) positioning a guide wire in said enlarged cavity, said guide wire having first and second separable sections, said guide wire extending from said distal end and out of said proximal end;

(c) positioning a dispenser containing bone graft material on said guide wire, said dispenser including an outlet and an elongated ejector member extending to an ejection end and having a passageway extending therethrough, said guide wire extending through said passageway and said outlet; and (d) moving said ejector member on said guide wire toward said outlet and said distal end to eject bone graft material through said outlet and into said enlarged cavity;

(e) separating said second section from said first section while leaving said first section positioned in said cavity; and (f) positioning a cannulated member having an elongated stem over said first section and into said cavity.

3. The method according to claim 2, further including extending said cannulated member distally into said cavity to compact said ejected bone graft material.

4. The method according to claim 2, wherein said ejector member includes an elongated portion and a first modular head defining an end having a first size and further including the step of replacing said first modular head on said elongated portion with a second modular head defining an end with a second size different from said first size and compacting said bone graft material with said second modular head.

5. A method for preparing a cavity in a long bone for receiving a prosthesis having an elongated stem comprising:

(a) forming an enlarged cavity extending from a distal end to a proximal end of said long bone;

(b) positioning a dispenser containing bone graft material at said proximal end, said dispenser including an outlet overlying said cavity and an elongated ejector member having a first modular head defining an end having a first size;

(c) moving said ejector member toward said outlet and said distal end to eject bone graft material through said outlet and into said cavity;

(d) replacing said first modular head on said ejector member with a second modular head defining an end with a second size different than said first size; and (e) moving said ejector member toward said outlet and said distal end to (1) eject bone graft material through said outlet and into said cavity and (2) compact said bone graft material.

6. Apparatus for dispensing bone graft material into an enlarged cavity of a long bone comprising:

(a) a body having a chamber for containing bone graft material, said body having an outlet and an aperture aligned with said outlet; and (b) an ejector member extending through said aperture and having (1) an elongated portion with a passageway extending therethrough for receiving a guide wire positioned in said cavity, (2) a first removable modular head having a first size and (3) a second removable modular head having a second size different than said first size, said ejector member being moveable (1) from a position at which said first head is positioned within said body, (2) to a position extending through said outlet to eject bone graft material therefrom and (3) to a position at which said first head can be removed and said second head engaged.

7. The apparatus for dispensing bone graft material according to claim 6, wherein said body includes a barrel extending along an axis disposed at an angle relative to the alignment of said aperture and outlet, said barrel having an outwardly extending offset encircling said aperture, said offset defining a cavity within said barrel to receive said first head.

8. Apparatus for dispensing bone graft material into an enlarged cavity of a long bone comprising:

(a) a body extending along a first axis and having a chamber for containing bone graft material, said body having an annular wall encircling said first axis and an outlet in said annular wall;

(b) a plunger positioned in said body for movement along said first axis, said plunger having an enlarged head moveable from a position axially spaced from said outlet to a position closer to said outlet;

(c) an ejector member having (1) an elongated portion extending along a second axis and having a passageway extending therethrough for receiving a guide wire, (2) a first removable modular head with a first size and (3) a second removable head with a second size larger than said first size, said ejector member being moveable (1) from a position at which said first head is positioned within said body, (2) to a position extending through said outlet to eject bone graft material therefrom and (3) to a position at which said first head can be removed and said second head engaged; and (d) a guide wire positioned in said passageway.

9. The apparatus for dispensing bone graft material according to claim 8, wherein said guide wire has first and second separable sections.

10. The apparatus for dispensing bone graft material according to claim 8, wherein said annular wall is provided with an outwardly extending offset encircling said aperture, said offset defining a cavity within said barrel to receive said first head.

11. Apparatus for dispensing bone graft material according to claim 8, wherein said barrel is provided with a gripping member engageable with said bone.

12. Apparatus for dispensing bone graft material according to claim 11, wherein said gripping member includes a pair of spaced apart elements.

13. Apparatus for dispensing bone graft material according to claim 12, wherein said spaced apart elements are fixed.

14. Apparatus for dispensing bone graft material according to claim 12, wherein one of said spaced apart elements is moveable about a pivot point.

15. Apparatus for dispensing bone graft material according to claim 14, wherein said moveable element has a gripping portion yieldingly urged toward the other of said spaced apart elements.

16. Apparatus for dispensing bone graft material according to claim 14, wherein said moveable element has a gripping portion on one side of said pivot point and a lock member on the opposite side of said pivot point for moving said gripping portion toward the other of said spaced apart elements.

17. Apparatus for dispensing bone graft material into an enlarged cavity of a long bone comprising:

(a) a body extending along a first axis and having a chamber for containing bone graft material, said body having (1) an annular wall encircling said first axis and (2) an outlet and an aperture in said annular wall cooperating to define a second axis, said annular wall having an outwardly extending offset defining a cavity within said body communicating with said chamber; and (b) an ejector member having an elongated portion extending along said second axis and having a head, said ejector member being moveable from a position at which said head is positioned within said cavity to a position extending through said outlet to eject bone graft material therefrom.

18. Apparatus for dispensing bone graft material into an enlarged cavity of a long bone comprising:

(a) a body extending along a first axis and having a chamber for containing bone graft material, said body having an annular wall encircling said first axis, an outlet in said annular wall and a bone gripping member adjacent said outlet;

(b) a plunger positioned in said body for movement along said first axis, said plunger being moveable from a position axially spaced from said outlet to a position closer to said outlet; and (c) an ejector member extending along a second axis and having a head, said ejector member being moveable from a position at which said head is positioned within said body to a position extending through said outlet to eject bone graft material therefrom.

19. Apparatus for dispensing bone graft material according to claim 18, wherein said barrel is provided with a gripping member engageable with said bone.

20. Apparatus for dispensing bone graft material according to claim 19, wherein said gripping member includes a pair of spaced apart elements.

21. Apparatus for dispensing bone graft material according to claim 20, wherein said spaced apart elements are fixed.

22. Apparatus for dispensing bone graft material according to claim 20, wherein one of said spaced apart elements is moveable about a pivot point.

23. Apparatus for dispensing bone graft material according to claim 22, wherein said moveable element has a gripping portion yieldingly urged toward the other of said spaced apart elements.

24. Apparatus for dispensing bone graft material according to claim 22, wherein said moveable element has a gripping portion on one side of said pivot point and a lock member on the opposite side of said pivot point for moving said gripping portion toward the other of said spaced apart elements.

* * * * *